US010919998B2

(12) United States Patent
Jung et al.

(10) Patent No.: US 10,919,998 B2
(45) Date of Patent: Feb. 16, 2021

(54) COLOR-CONVERSION PHOTONIC CRYSTAL STRUCTURE AND COLOR-CONVERSION PHOTONIC CRYSTAL SENSOR USING SAME

(71) Applicant: KOREA RESEARCH INSTITUTE OF CHEMICAL TECHNOLOGY, Daejeon (KR)

(72) Inventors: Seo Hyun Jung, Ulsan (KR); Jong Mok Park, Daejeon (KR); Ho Youl Kong, Gyeongsangnam-do (KR); Ja Young Bae, Ulsan (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 365 days.

(21) Appl. No.: 15/776,257

(22) PCT Filed: Dec. 9, 2016

(86) PCT No.: PCT/KR2016/014471
§ 371 (c)(1),
(2) Date: May 15, 2018

(87) PCT Pub. No.: WO2017/099532
PCT Pub. Date: Jun. 15, 2017

(65) Prior Publication Data
US 2020/0255565 A1    Aug. 13, 2020

(30) Foreign Application Priority Data
Dec. 9, 2015  (KR) .................. 10-2015-0175283

(51) Int. Cl.
*C08F 212/12*      (2006.01)
*C08F 220/54*      (2006.01)
(Continued)

(52) U.S. Cl.
CPC .......... *C08F 212/12* (2013.01); *C08F 220/54* (2013.01); *G01N 21/81* (2013.01);
(Continued)

(58) Field of Classification Search
None
See application file for complete search history.

(56) References Cited

U.S. PATENT DOCUMENTS

2012/0293802 A1    11/2012  Ozin et al.
2016/0252625 A1    9/2016   Hayward et al.

FOREIGN PATENT DOCUMENTS

CN    103901536 A    7/2014
CN    105102692 A    11/2015
(Continued)

OTHER PUBLICATIONS

International Search Report for PCT/KR2016/014471.
Yetisen, Ali K. et al., "Photonic Hydrogel Sensors", Biotechnology Advances, vol. 34, pp. 250-271, Oct. 17, 2015.
Notice of Allowance dated Jun. 16, 2017 from Korean Patent Office in a counterpart Korean Patent Application No. 10-2015-0175283 (all the cited references are listed in this IDS.) (English translation is submitted herewith).
(Continued)

*Primary Examiner* — Fred M Teskin
(74) *Attorney, Agent, or Firm* — The PL Law Group, PLLC

(57) ABSTRACT

A photonic crystal structure employs such a structure that two layers having different refractive indices are laminated alternately, a polymer including a structure unit derived from a monomer that contains a fluorocarbon group being used for one of the repeated layers such that the photonic crystal structure can respond to humidity and/or organic solvent concentration. Using the photonic crystal structure, it is possible to manufacture a color-conversion photonic crystal sensor having excellent sensitivity and reproduction characteristics.

10 Claims, 2 Drawing Sheets

(51) Int. Cl.
   *G01N 21/81* (2006.01)
   *G02F 1/361* (2006.01)
   *B82Y 15/00* (2011.01)
   *B82Y 20/00* (2011.01)

(52) U.S. Cl.
   CPC ............ *G02F 1/3615* (2013.01); *B82Y 15/00* (2013.01); *B82Y 20/00* (2013.01); *G02F 2202/022* (2013.01); *G02F 2202/32* (2013.01)

(56) References Cited

FOREIGN PATENT DOCUMENTS

| | | | |
|---|---|---|---|
| JP | 2006-099049 A | 4/2006 | |
| JP | 2006-126680 A | 5/2006 | |
| JP | 2007-136822 A | 6/2007 | |
| JP | 2012-141459 A | 7/2012 | |
| KR | 10-2011-0050596 A | 5/2011 | |
| KR | 10-1098515 B1 | 12/2011 | |
| KR | 10-1381360 B1 | 4/2014 | |
| WO | 2010/078378 A1 | 7/2010 | |
| WO | 2013/123378 A1 | 8/2013 | |
| WO | 2014/154557 A1 | 10/2014 | |
| WO | 2015/178391 A1 | 11/2015 | |

OTHER PUBLICATIONS

Maria C. Chiappelli et al., "Photonic multilayer sensors from photo-crosslinkable polymer films", Advanced Materials, vol. (24), Sep. 2012. (Abstract is submitted herewith).

Office action dated Apr. 23, 2019 from China Patent Office in a counterpart China Patent Application No. 201680071195.6 (all the cited references are listed in this IDS.) (English translation is also submitted herewith.).

European Search Report for EP 16873397.0 dated May 16, 2019 from European patent office in a counterpart European patent application.

Office action dated Jun. 25, 2019 from Japan Patent Office in a counterpart Japan Patent Application No. 2018-529238 (all the cited references are listed in this IDS.) (English translation is also submitted herewith.).

Zhanhua Wang et al., "Polymer Bragg stack as color tunable photonic paper", Journal of Materials Chemistry, vol. 22, No. 16, 2012.

Jae Min Bak, et al., "Novel Thermoresponsive Fluorinated Double-Hydrophilic Poly {[N-(2,2-difluoroethyl)acrylamide]-b-[N-(2-fluoroethyl)acrylamide]} Block Copolymers", Journal of Polymer Science, Part A: Polymer Chemistry, vol. 51, 2013.

COLOR-CONVERSION PHOTONIC CRYSTAL STRUCTURE AND COLOR-CONVERSION PHOTONIC CRYSTAL SENSOR USING SAME

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2016/014471, filed Dec. 9, 2016, which claims priority to the benefit of Korean Patent Application No. 10-2015-0175283 filed in the Korean Intellectual Property Office on Dec. 9, 2015, the entire contents of which are incorporated herein by reference.

TECHNICAL FIELD

The present invention relates to a color-conversion photonic crystal structure and a color-conversion photonic crystal sensor using the same, and more particularly, to a color-conversion photonic crystal structure responding to humidity and/or organic solvents and a color-conversion photonic crystal sensor using the same.

BACKGROUND ART

A photonic crystal is a structure in which dielectric substances having different refractive indices are periodically aligned, and refers to a material to selectively reflect light while preventing light transmission in a specific wavelength range since overlapping interference occurs between lights scattered at separate and regular lattice points, that is, a material for forming a light band gap.

The photonic crystal as described above uses photons instead of electrons as a means for processing information and exhibits an excellent information processing rate, thereby rising as an essential material for improving efficiency of information-oriented industry. Further, the photonic crystal may be achieved in any of a one-dimensional structure in which photons move in a primary axial direction, a two-dimensional structure in which photons move along a plane, or a three-dimensional structure in which photons freely move in all directions throughout the material. Further, optical characteristics may be easily controlled by adjusting a light band gap, thereby being applicable in various fields. For example, the photonic crystal may be applied in optical elements such as photonic crystal fibers, light emitting elements, photovoltaic devices, photonic crystal sensors, semiconductor lasers, and the like.

In particular, Bragg stack is a photonic crystal having one-dimensional structure, and may be easily fabricated only by laminating two layers having different refractive indices, as well as has an advantage of easily controlling optical characteristics by regulating the refractive indices of these two layers and adjusting thicknesses thereof. Due to such characteristics, the Bragg stack has been widely used in not only energy elements such as a solar cell but also a photonic crystal sensor for detecting electrical, chemical or thermal stimulation. Therefore, diverse substances and structures for easily manufacturing the photonic crystal sensor with excellent sensitivity and reproducibility have been currently studied.

Accordingly, as a result of extensive efforts, the present inventors have found that, when using a polymer having a structure unit derived from a monomer containing a fluorinated carbon group used for one of repeated layers in the Bragg stack, it is possible to easily manufacture a color-conversion photonic crystal structure which exhibits a color change depending on a change in humidity and/or organic solvent concentration, as well as a photonic crystal sensor using the same, which exhibits excellent sensitivity and reproducibility, and therefore, the present invention has been completed on the basis of the above finding.

SUMMARY

It is an object of the present invention to provide a color-conversion photonic crystal structure responding to humidity and/or organic solvent.

In addition, another object of the present invention is to provide a color-conversion photonic crystal sensor using the same, which has excellent sensitivity and reproducibility.

In order to accomplish the above-described objects, the present invention provides a color-conversion photonic crystal structure, including: a first refractive index layer which includes a first polymer having a first refractive index; and a second refractive index layer which includes a second polymer having a second refractive index, wherein these refractive index layers are alternately laminated, wherein the first refractive index and the second refractive index are different from each other, and one of the first polymer and the second polymer is a polymer having a structure unit derived from a monomer containing a fluorinated carbon group.

In addition, the present invention provides a color-conversion photonic crystal sensor including the above color-conversion photonic crystal structure.

The color-conversion photonic crystal structure of the present invention includes a low refractive index layer formed of a polymer having a structure unit derived from a monomer containing a fluorinated group ('a fluorinated carbon group-containing monomer'), such that colors thereof may be converted to be visibly determined depending on a change in humidity and/or organic solvent concentration. Further, the color-conversion photonic crystal sensor using the above color-conversion photonic crystal structure may achieve excellent sensitivity and reproducibility.

DETAILED DESCRIPTION

Figure 1:
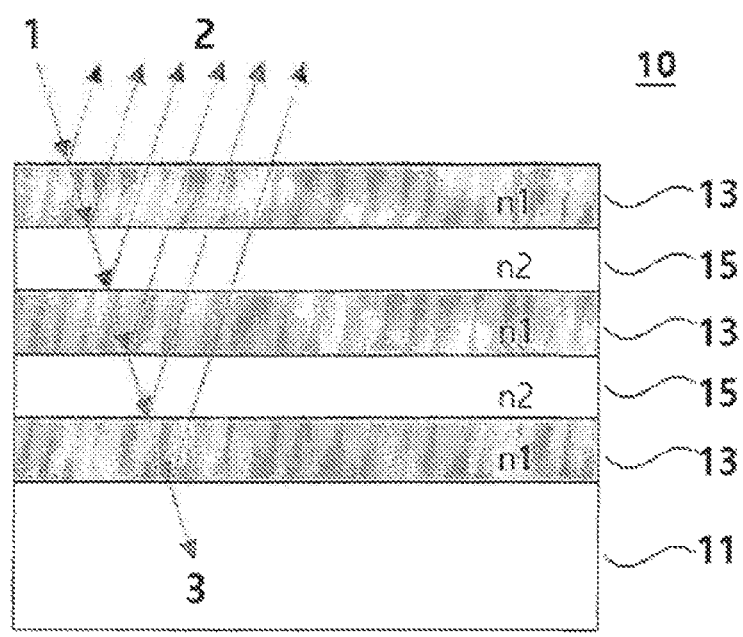
FIG. 1 is a schematic view illustrating a construction of a color-conversion photonic crystal structure according to one embodiment of the present invention.

A color-conversion photonic crystal structure of the present invention includes: a first refractive index layer which includes a first polymer having a first refractive index; and a second refractive index layer which includes a second polymer having a second refractive index, wherein these refractive index layers are alternately laminated, wherein the first refractive index and the second refractive index are different from each other, and one of the first polymer and the second polymer is a polymer having a structure unit derived from a monomer containing a fluorinated carbon group.

In addition, a color-conversion photonic crystal sensor of the present invention includes the above color-conversion photonic crystal structure.

In the present invention, the terms "the first and the second, etc." are used for describing various components, and these terms are used for the purpose of distinguishing one component from other components only.

In addition, the terminology used in the present disclosure is for the purpose of describing particular embodiments only and is not intended to limit the present invention thereto. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Further, in the present invention, when describing in such a way that a layer or element is formed "on" or "above" another layer(s) or element(s), this means that a layer or element is directly formed on another layer(s) or element(s), or otherwise, another layer or element may be further formed between layers, subjects or substrates.

The present invention may be altered in various ways and have various embodiments, and will be described with reference to the drawings for illustrating specific embodiments. However, the present invention is not limited to the specific embodiments, and it will be understood by those skilled in the art that the invention is to cover all modifications, equivalents, and alternatives falling within the spirit and scope of the invention.

Hereinafter, some terms used in the present disclosure may be defined as follows.

First, the term "color-conversion photonic crystal structure" used herein refers to Bragg stack with an one-dimensional structure formed by repeatedly laminating substances having different refractive indices, alternately, wherein the stack may reflect light in a specific wavelength range due to a periodical difference in the refractive indices of the laminated structure, and such reflective wavelength is shifted by an external stimulation to convert the reflected color. In particular, the light is partially reflected at an interface between layers of the structure, and many reflected waves may structurally interfere to one another so as to reflect light having a high-intensity at a specific wavelength. Herein, the shift of the reflective wavelength due to the external stimulation occurs while a wavelength of scattered light is altered by a change in a lattice structure of a layer-formable substance due to the external stimulation. Such a color-conversion photonic crystal structure may be manufactured in a form of a coating film on an alternative substrate or board, or a form of a free-standing film. Further, the color-conversion photonic structure may be applied to a photonic crystal fiber or optical devices such as a light emitting element, photovoltaic device, photonic crystal sensor, semiconductor laser, and the like. For example, the color-conversion photonic crystal structure may be employed in optical sensors such as an environmental device for detection of chemical and biological species, or bio-sensors such as a glucose sensor, protein sensor, DNA sensor, disease diagnostic sensor, portable diagnostic sensor, etc., but it is not limited thereto in terms of applicable fields.

Meanwhile, according to one embodiment of the present invention, the color-conversion photonic crystal structure may include: a first refractive index layer including a first polymer having a first refractive index; a second refractive index layer including a second polymer having a second refractive index, wherein these layers are alternately laminated. In this case, the first refractive index and the second refractive index may be different from each other, and one of the first polymer and the second polymer may be a polymer containing a structural unit derived from a fluorinated carbon group-containing monomer.

A total number of the laminated first and second refractive index layers may range from 5 to 30. In a case of the structure having the refractive index layers laminated within the above range, lights reflected at the interfaces between the respective layers may sufficiently interfere to one another, thus to have a desired reflective intensity enough to detect a color change due to an external stimulation.

In this regard, the first refractive index layer may be located on the uppermost part of the color-conversion photonic crystal structure. Therefore, the first refractive index layer may be further laminated on a laminate in which first refractive index layer and second refractive index layer are alternately laminated, such that the photonic crystal structure may have an odd number of the refractive index layers. In this case, constructive interference between lights reflected at the interfaces between the respective layers is increased, thus to increase an intensity of the reflective wavelength of the photonic crystal structure, as described below.

Further, a thickness of the first refractive index layer in the color-conversion photonic crystal structure may range from 50 to 150 nm, while a thickness of the second refractive index layer may range from 5 to 80 nm. For example, a ratio of the thickness of the first refractive index layer to the thickness of the second refractive index layer may range from 1:1 to 3:1. By adjusting the thicknesses of theses layers within the above ranges, a reflective wavelength of the photonic crystal structure may be controlled, as described below.

Hereinafter, a schematic construction of a color-conversion photonic crystal structure 10 according to one embodiment will be described in detail with reference to FIG. 1.

Referring to FIG. 1, the color-conversion photonic crystal structure 10 according to one embodiment may include: a substrate 11; and a first refractive index layer and a second refractive index layer 15 which are alternately laminated on the substrate 11. When a multi-colored white light including all colors, which are in equal proportion, enters the color-conversion photonic crystal structure 10, incident light is partially reflected at the interfaces between the respective layers such that a part of the incident light becomes a reflected light 2 while the other part thereof is present as a transmitted light 3. That is, due to the interference between such the partially reflected lights, lights at specific wavelengths concentrated around a wavelength A are reflected. When the reflective wavelength A is within a visible light region, colors reflected by the photonic crystal structure may be determined.

Herein, when the color-conversion photonic crystal structure 10 is located in an environment undergoing an external stimulation, crystal lattice structures of the first and second polymers, which are included in the first refractive index layer 13 and the second refractive index layer 15, respectively, are changed. For this reason, a form of scattering at the interfaces between the respective layers is changed, such that the photonic crystal structure reflects a light having a shifted wavelength A'. Therefore, as compared to a case in which an external stimulation is not applied, the color expressed by the photonic crystal structure may be converted. If the external stimulation is high, an intensity of the change in the crystal lattice structure of the first and second polymers is increased, and the reflective wavelength is further shifted. As a result, the intensity of the external stimulation may be detected depending on the expressed color.

Meanwhile, FIG. 1 illustrates a photonic crystal structure consisting of 5 layers only, however, the number of the laminated layers in the photonic crystal structure is not limited thereto. Further, a structure, in which the refractive index layers are laminated on the substrate 11, has been described, however, a free-standing film type structure without the substrate 11 may also be possible.

The substrate 11 may include a carbon material substrate, metal foil, thin glass or plastic substrate having an excellent mechanical strength, thermal stability, transparency, surface smoothness, easy management and waterproofing property, but it is not limited thereto. Further, the substrate 11 may also include a substrate made using various flexible or inflexible substances.

The first refractive index layers 13 alternately laminated on the substrate 11 may include a first polymer with a first refractive index n1, while the second refractive index layer 15 may include a second polymer with a second refractive index n2. Herein, a difference between the first refractive index n1 and the second refractive index n2 may range from 0.01 to 0.5. For example, a difference between the first refractive index n1 and the second refractive index n2 may range from 0.05 to 0.3, in particular, from 0.1 to 0.2. As the difference between these two refractive indices is increased, a light band gap in the photonic crystal structure is also increased. Therefore, by adjusting the difference between the refractive indices within the above range, the photonic crystal structure may be controlled so as to reflect a light with a desired wavelength.

For example, the first refractive index n1 may be larger than the second refractive index n2. In other words, the photonic crystal structure 10 may have a construction in which high refractive index layer/low refractive index layer/high refractive index layer/low refractive index layer/high refractive index layer are sequentially laminated on the substrate 11.

Alternatively, the first refractive index n1 may be smaller than the second refractive index n2. In other words, the photonic crystal structure 10 may have a construction in which low refractive index layer/high refractive index layer/low refractive index layer/high refractive index layer/low refractive index layer sequentially laminated on the substrate 11.

In this regard, the low refractive index layer may have a refractive index of 1.3 to 1.5, while the high refractive index layer may have a refractive index of 1.51 to 1.8. Within the above ranges, a photonic crystal structure capable of reflecting a light with the desired wavelength may be achieved.

More particularly, the first refractive index layer 13 of the photonic crystal structure 10 may be a high refractive index layer including a first polymer, which has a thickness of 50 to 150 nm and a first refractive index of 1.51 to 1.8 and; and a second refractive index layer 15 may be a low refractive index layer including a second polymer, which has a thickness of 5 to 80 nm and a refractive index of 1.3 to 1.5.

One of the first refractive index layer and the second refractive index layer, which has the lower refractive index, may include a polymer having a repeat unit derived from a fluorinated carbon group-containing monomer. For example, the above polymer may include 98 to 99.5% by weight ('wt. %') of repeat unit derived from the fluorinated carbon group-containing monomer. Herein, the 'fluorinated carbon group-containing monomer' refers to a monomer containing at least one double bond cross-linkable by light irradiation as well as at least one fluorinated carbon group. Further, the 'fluorinated carbon group' means a functional group in which at least one fluorine atom is bonded to a carbon atom. Such a functional group may be located not only at an end of a molecule but also at a side chain thereof. Furthermore, two or more fluorine atoms may be bonded to a single carbon atom or a plurality of carbon atoms. Particular examples of the fluorinated carbon group may include fluoromethyl, difluoromethyl, trifluoromethyl, fluoroethyl, difluoroethyl and trifluoroethyl groups, but it is not limited thereto.

A polymer having a structure unit derived from the fluorinated carbon group-containing monomer has a lower refractive index than the polymers containing different functional groups, and therefore, may form a low refractive index layer having a refractive index within the above defined range. Further, such a low refractive index layer may exhibit excellent chemical and physical properties and superior transparency. Accordingly, the polymer having a structure unit derived from the fluorinated carbon group-containing monomer has a lower refractive index than the polymers without the structure unit, thereby forming a low refractive index layer.

The fluorinated carbon group-containing monomer may further contain an amide group. For example, the fluorinated carbon group-containing monomer may be an acrylamide compound containing a fluorinated carbon group. A polymer having a repeat unit derived from the acrylamide compound containing a fluorinated carbon group may be easily swollen thus to shift the reflective wavelength of the photonic crystal structure due to the external stimulation such as moisture and/or a change in a concentration of an organic solvent, and may rapidly return the same to its original state if the external stimulation is stopped. Therefore, it is possible to improve reproducibility of the color-conversion sensor. Swelling of the polymer may occur by a hydrogen bond between acrylamide and moisture and/or an organic solvent. In particular, the fluorinated carbon group-containing monomer may include at least one selected from a group consisting of N-(2-fluoroethyl)acrylamide, N-(2,2-difluoroethyl) acrylamide and N-(2,2,2-trifluoroethyl) acrylamide.

Therefore, when the first refractive index layer 13 of the photonic crystal structure 10 is a high refractive index layer and the second refractive index layer 15 is a low refractive index layer, the second polymer may be a polymer having a structure unit derived from the fluorinated carbon group-containing monomer.

In this regard, the first polymer may have a structure unit derived from the following monomers and may have a higher refractive index than the second polymer: (meth) acrylate, (meth)acrylamide, an aromatic compound containing a vinyl group, dicarboxylic acid, xylylene, alkylene oxide, arylene oxide and derivatives thereof, which may be used alone or in combination of two or more thereof.

For example, the first polymer may have one or two or more structure units derived from the following monomers: acryl-based monomer such as methyl (meth)acrylate, ethyl (meth)acrylate, isobutyl (meth)acrylate, 1-phenylethyl (meth)acrylate, 2-pheylethyl (meth)acrylate, 1,2-diphenylethyl (meth)acrylate, phenyl (meth)acrylate, benzyl (meth) acrylate, m-nitrobenzyl (meth)acrylate, β-naphthyl (meth) acrylate, benzoylphenyl (meth)acrylate, etc.; (meth) acrylamide-based monomer such as methyl (meth) acrylamide, ethyl (meth)acrylamide, isobutyl (meth)

acrylamide, 1-phenylethyl (meth)acrylamide, 2-phenylethyl (meth)acrylamide, phenyl (meth)acrylamide, benzyl (meth)acrylamide, benzoylphenyl (meth)acrylamide, etc.; styrene-based monomer such as styrene, o-methylstyrene, m-methylstyrene, p-methylstyrene, p-methoxystyrene, o-methoxystyrene, 4-methoxy-2-methylstyrene, etc.; aromatic monomer such as p-divinylbenzene, 2-vinylnaphthalene, vinylcarbazole, vinylfluorene, etc.; dicarboxylic acid monomer such as terephthalic acid, isophthalic acid, 2,6-naphthalene dicarboxylic acid, 2,7-naphthalene dicarboxylic acid, 1,4-naphthalene dicarboxylic acid, 1,4-phenylene dioxyphenylic acid, 1,3-phenylene dioxydiacetic acid, etc.; xylylene-based monomer such as o-xylylene, m-xylylene, p-xylylene, etc.; alkylene oxide-based monomer such as ethylene oxide, propylene oxide, etc.; phenylene oxide-based monomer such as phenylene oxide, 2,6-dimethyl-1,4-phenylene oxide, etc. Among these, in terms of preferred difference in the refractive indices and easy photo-curing, the first polymer preferably has a structure unit derived from the styrene-based monomer and a structure unit derived from one of (meth)acrylate or (meth)acrylamide.

In particular, the first polymer may have a structure unit represented by Formulae 1 and 2 below in a molar ratio of 100:1 to 100:20, and a number average molecular weight Mn of 10,000 to 100,000 g/mol. Otherwise, the first polymer may have a structure unit represented by Formulae 1 and 2 below in a molar ratio of 100:1 to 100:10, and a number average molecular weight Mn of 10,000 to 50,000 g/mol.

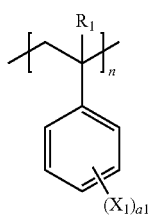

[Formula 1]

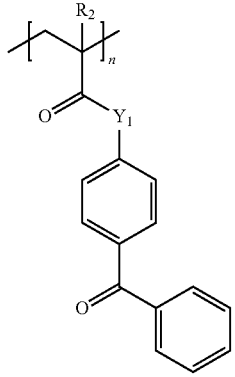

[Formula 2]

In Formulae 1 and 2, $R_1$ and $R_2$ may be each independently selected from hydrogen and $C_{1-3}$ alkyl. For example, $R_1$ and $R_2$ may be hydrogen, respectively.

In Formula 1, $X_1$ may be selected from hydroxyl, cyano, nitro, amino, sulphonic acid or salts thereof, $C_{1-10}$ alkyl and $C_{1-10}$ alkoxy. In particular, $X_1$ in Formula 1 may be selected from methyl, ethyl, propyl, butyl, iso-butyl, sec-butyl and tert-butyl. More particularly, $X_1$ may be methyl. For example, $X_1$ may be para-methyl.

In Formula 1, a1 may be selected from 0, 1, 2, and 3. a1 denotes the number of $X_1$ and, when a1 is 2 or more, two or more $X_1$ may be the same as or different from one another. For example, a1 may be 0 or 1.

In Formula 2, $Y_1$ may be O or NH.

Further, in Formulae 1 and 2, n may be independently an integer of 1 or more.

The second polymer may have a structure unit represented by Formulae 3 and 4 below in a molar ratio of 100:1 to 100:5, and a number average molecular weight of 10,000 to 100,000 g/mol. Otherwise, the second polymer may have a structure unit represented by Formulae 3 and 4 below in a molar ratio of 100:1 to 100:3, for example, 100:1 to 100:5, and a number average molecular weight of 10,000 to 80,000 g/mol.

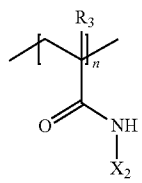

[Formula 3]

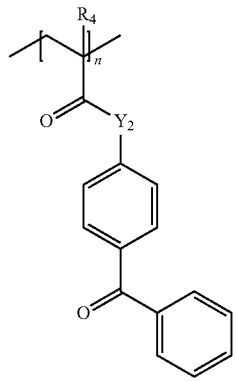

[Formula 4]

In Formulae 3 and 4, $R_3$ and $R_4$ may be each independently selected from hydrogen and $C_{1-3}$ alkyl. For example, $R_3$ and $R_4$ may be hydrogen, respectively.

In Formula 3, $X_2$ may be selected from $C_{1-10}$ alkyl substituted by at least one fluorine atom. For example, $X_2$ may be selected from $C_{1-3}$ alkyl substituted by at least one fluorine atom. In particular, $X_2$ may be selected from fluoromethyl, difluoromethyl, trifluoromethyl, 1-fluoroethyl, 2-fluoroethyl, 1,1-difluoroethyl, 1,2-difluoroethyl, 2,2-difluoroethyl, 1,1,2-trifluoroethyl, 1,2,2-trifluoroethyl, 2,2,2-trifluoroethyl, 1-fluoropropyl, 2-fluoropropyl, 1,1-difluoropropyl, 1,2-difluoropropyl, 2,2-difluoropropyl, 1,1,2-trifluoropropyl, 1,2,2-trifluoropropyl, 2,2,2-trifluoropropyl, 1-fluorobutyl, 2-fluorobutyl, 1,1-difluorobutyl, 1,2-difluorobutyl, 2,2-difluorobutyl, 1,1,2-trifluorobutyl, 1,2,2-trifluorobutyl and 2,2,2-trifluorobutyl.

In Formula 4, $Y_2$ may be O or NH.

Further, in Formulae 3 and 4, n may be independently an integer of 1 or more.

Herein, each of the first polymer and the second polymer may be a random copolymer having a structure unit randomly arranged therein, or a block copolymer having structure units repeatedly arranged by predetermined number of repeating times, but it is not limited thereto in terms of the arrangement form.

When the first polymer has the structure unit represented by Formula 1 within the above defined range, it is possible to have a higher refractive index than the second polymer having a structure unit derived from the monomer containing a fluorinated carbon group (that is, the structure unit represented by Formula 3). Further, due to an appropriate difference in the refractive indices, it is possible to achieve the desired reflective wavelength in the photonic crystal structure.

Further, the first polymer and the second polymer may have the structure units represented by Formulae 2 and 4 within the above-described range, respectively, wherein such structure units may be derived from benzophenone acrylamide-based monomer. When using such a benzophenone acrylamide-based monomer, the polymer may be self-photocured without separate photo-initiator or cross-linker, thereby being advantageous in an aspect of easy photocuring.

More particularly, the first polymer may have a structure unit represented by one of Formulae 1-1 and 2-1, while the second polymer may have a structure unit represented by one of Formulae 3-1 to 3-3 as well as Formula 2-1.

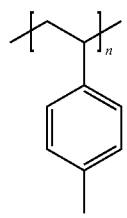

[Formula 1-1]

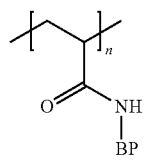

[Formula 2-1]

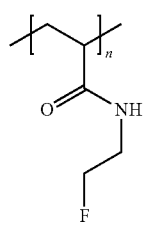

[Formula 3-1]

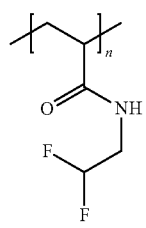

[Formula 3-2]

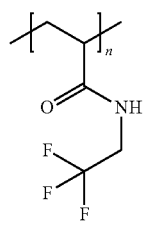

[Formula 3-3]

In Formula 2-1, BP denotes 4-benzoylphenyl.

Among these, when the second polymer have a structure unit represented by one of Formulae 3-1 and as well as Formula 2-1, the polymer may be easily swollen by moisture penetrated from an outside, thereby easily manufacturing a sensor for detecting moisture.

Alternatively, the first refractive index layer 13 may be a low refractive index layer while the second refractive index layer 15 may be a high refractive index layer. In this case, the first polymer and the second polymer may be reversely used.

With regard to the color-conversion photonic crystal structure 10 according to one embodiment of the present invention, the reflective wavelength λ thereof may be determined by Mathematical Equation 1 below.

$$\lambda = 2(n1*d1 + n2*d2)$$ <Mathematical Equation 1>

Wherein n1 and n2 refer to refractive indices of the first refractive index layer 13 and the second refractive layer 15, respectively; d1 and d2 refer to thicknesses of the first refractive index layer 13 and the second refractive index layer 15, respectively. Therefore, in order to shift the reflective wavelength λ of the color-conversion photonic crystal structure 10, not only types of the polymer but also thicknesses of the first refractive index layer 13 and the second refractive index layer 15 may be adjusted.

The color-conversion photonic crystal structure 10 according to one embodiment may have a reflective wavelength λ in a range of 200 to 760 nm by the above Mathematical Equation 1.

The reflective wavelength of the above-described photonic crystal structure 10 may be shifted by an external stimulation. More particularly, the reflective wavelength of the photonic crystal structure 10 may be shifted by swelling first polymer and second polymer due to the external stimulation. In particular, a reflective wavelength λ' shifted by the external stimulation may correspond to visible light region visually recognized by an operator. For example, the reflective wavelength λ' shifted by the external stimulation may range from 380 to 760 nm. Both the reflective wavelength λ and the shifted reflective wavelength λ' may be measured by an apparatus such as a reflectometer.

In this regard, the external stimulation may include chemical stimulation, for example, stimulation caused by a change in a concentration of a chemical substance. More particularly, the external stimulation may be caused by a change in humidity or organic solvent concentration. For example, the organic solvent may include a polar organic solvent which is able to couple with an amide group in the fluorinated carbon group-containing monomer by a hydrogen bond. More particularly, the organic solvent may include, for example: alcohols such as methanol, ethanol, 1-propanol, isopropanol, butanol, 2-ethoxy ethanol, 2-butoxy ethanol, 2-methoxy propanol, etc.; ketones such as acetone, methylethylketone, etc.; 2-pyrrolidone, N-methyl-2-pyrrolidone (NMP), N-vinyl-2-pyrrolidone (NVP), dimethyl sulfoxide (DMSO), dimethyl formamide (DMF), or the like, but it is not limited thereto. In particular, the color-conversion photonic crystal structure may respond to the external stimulation caused by a change in humidity and/or a change in a concentration of alcohol such as methanol, ethanol, etc. with high sensitivity.

An amount shifting the reflective wavelength λ' may depend on an intensity of the external stimulation. More particularly, when the intensity of the external stimulation is increased, for example, with the humidity or concentration of the organic solvent is increased, the reflective wavelength of the photonic crystal structure may be increased.

The color-conversion photonic crystal structure as described above may be prepared by a manufacturing method including the following steps:

(1) preparing a first refractive index layer using a first dispersion composition that includes a first polymer having a first refractive index;

(2) preparing a second refractive index layer on the first refractive index layer using a second dispersion composition that includes a second polymer having a second refractive index; and (3) alternately laminating the first refractive index layer and the second refractive index layer to form a photonic crystal structure in which 5 to 30 layers are alternately laminated.

According to the method for manufacturing a color-conversion photonic crystal structure, details of the first refractive index, the first polymer, the second refractive index, the second polymer, the first refractive index layer and the second refractive index layer are substantially the same as the above description.

First, the first dispersion composition and the second dispersion composition may be prepared. Each of these dispersion compositions may be prepared by dispersing polymers in the organic solvent. Herein, the term 'dispersion composition' means various phases such as a solution, slurry or paste phase. In this regard, each of the first and second polymers may be included in an amount of 0.5 to 5 wt. % to a total weight of the dispersion composition. Within the above range, a dispersion composition having a viscosity suitable to be applied to the substrate may be prepared.

For example, the first dispersion composition may include an organic solvent as well as a first polymer, while the second dispersion composition may include an organic solvent as well as a second polymer. In other words, alternative photo-initiator for photocuring and cross-linker, or inorganic particles may not be included. Therefore, the photonic crystal structure may be more easily and economically manufactured. Further, since any alternative additive is not included, a deviation in photonic characteristics depending on a location of the manufactured photonic crystal structure may be reduced.

Next, after applying the prepared first dispersion composition to the substrate or board, light irradiation may be conducted to form a first refractive index layer. Thereafter, after applying the prepared second dispersion composition to the first refractive index layer, light irradiation may be conducted again to form a second refractive index layer.

In this regard, a method of applying the dispersion composition to the substrate or the refractive index layer may include, for example, spin coating, dip coating, roll coating, screen coating, spray coating, spin casting, flow coating, screen printing, ink jet or drop casting, etc., but it is not limited thereto.

The light irradiation may be performed by irradiating the substrate with light at a wavelength of 365 nm under a nitrogen condition. Benzophenone moiety contained in the polymer may function as a photo-initiator by the light irradiation, thereby forming the photo-cured refractive index layer.

Meanwhile, according to another embodiment of the present invention, there is provided a color-conversion photonic crystal sensor including the color-conversion photonic crystal structure described above.

The color-conversion photonic crystal sensor may be used for detecting humidity or organic solvent since a reflective wavelength of the color-conversion photonic crystal structure is shifted according to the change in humidity or organic solvent concentration. Further, the color-conversion photonic crystal sensor is able to detect not only the existence of substances that should be detected such as moisture and the organic solvent, but also concentrations of the substances, thereby being useful for all of qualitative and quantitative analyses. Further, for the reasons as described above, the color-conversion photonic crystal sensor using the photonic crystal structure according to one embodiment of the present invention may accomplish excellent sensitivity and superior reproducibility.

Hereinafter, operations and functional effects of the present invention will be described in more detail with reference to following particular examples. However, such examples are proposed for the illustrative purposes and do not limit the scope of the present invention, which are defined only by the appended claims and their equivalents.

Materials to be Used

The following materials were used in preparative examples below. Herein, these materials were used without any alternative purification process.

4-Aminobenozophenone: a product with 98% purity manufactured by Tokyo Chemical Industry (TCI) Co.

Triethylamine: a product with 99% purity manufactured by TCI Co.

Dichloromethane: a product with 99.9% purity manufactured by Burdick & Jackson Co.

Acryloyl chloride: a product with 96% purity manufactured by Merck Co.

Tetrahydrofuran: a product with 99.99% purity manufactured by Burdick & Jackson Co.

p-Methylstyrene: a product with 96% purity manufactured by Sigma-Aldrich Co.

Azobisisobutyronitrile: a product with 98% purity manufactured by JUNSEI Co.

N-Isopropyl acrylamide: a product with 98% purity manufactured by TCI Co.

Notation of Monomer and Copolymer

Names and notations of the monomer and the copolymer prepared in the following preparative examples are as follows:

TABLE 1

| | Name | Notation |
|---|---|---|
| Preparative Example 1 | N-(4-benzoylphenyl)acrylamide | BPAA |
| Preparative Example 2 | N-(2-fluoroethyl)acrylamide | FEAA |
| Preparative Example 3 | N-(2,2-difluoroethyl)acrylamide | DFEAA |
| Preparative Example 4 | N-(2,2,2-trifluoroethyl)acrylamide | TFEAA |
| Preparative Example 5 | Poly(para-methylstyrene)-co-(N-(4-benzoylphenyl)acrylamide) | Poly (p-MS-BPAA) |
| Preparative Example 6 | Poly(N-(2-fluoroethyl)acrylamide)-co-N-(4-benzoyl-phenyl)acrylamide) | Poly (FEAA-BPAA) |
| Preparative Example 7 | Poly(N-(2,2-difluoroethyl)acrylamide)-co-(N-(4-benzoyl-phenyl)acrylaamde) | Poly (DFEAA-BPAA) |
| Preparative Example 8 | Poly(N-(2,2,2-trifluoroethyl)acrylamide)-co-(N-(4-benzoyl-phenyl)acrylamide) | Poly (TFEAA-BPAA) |

EXAMPLE

Synthesis of Monomer

Preparative Example 1: Preparation of BPAA

After adding 9.96 g of 4-aminobenzophenone, 7 mL of triethylamine and 80 mL of dichloromethane to a 250 mL round flask, the flask was placed in ice water. After diluting 4.06 mL of acryloyl chloride in 8 mL of dichloromethane, this solution was slowly added drop wise to the flask, followed by agitating the same for 12 hours. After completing the reaction, unreacted material and salts were removed with a saturated solution containing 5% $NaHCO_3$ and sodium chloride using a separatory funnel, and then, excess water was removed from an organic layer using $NaSO_4$ anhydride. Subsequently, after removing the solvent by a rotary evaporator, the remaining solution was dried in a vacuum oven at room temperature, thereby obtaining N-(4-benzoylphenyl)acrylamide as a yellow solid.

Preparative Example 2: Preparation of FEAA 10 g of 2-fluoroethylamine was added along with 20 ml of distilled water to a round-bottomed flask, followed by neutralization and then extraction with dichloromethane. The extracted organic solvent layer was concentrated by a rotary evaporator after removing the remaining water using $MgSO_4$. After adding 12 mL of triethylamine to the concentrated sample, the flask was placed in ice water. After diluting 7.7 mL of acryloyl chloride in 10 mL of dichloromethane, this solution was slowly added drop wise to the flask while agitating the same. After completely adding the diluted solution thereto, the mixture was agitated at room temperature for 12 hours. After completing the reaction, the precipitate was filtered and the solution was concentrated by the rotary evaporator. The concentrated sample was subjected to column chromatography with Hexane:Ethyl acetate to separate N-(2-fluoroethyl)acrylamide only, and then, the solvent was removed by the rotary evaporator, thereby obtaining pure N-(2-fluoroethyl)acrylamide as a pale yellow liquid.

Preparative Example 3: Preparation of DFEAA

After adding 8.67 mL of 2,2-difluoroethylamine, 20.5 ml of triethylamine and 100 mL of tetrahydrofuran to an one-neck round flask, the flask was placed in ice water. After diluting 12 mL of acryloyl chloride in 10 mL of tetrahydrofuran, this solution was slowly added drop wise to the flask while agitating the same. After completely adding the diluted solution thereto, the mixture was agitated at room temperature for 12 hours. After completing the reaction, the precipitate was filtered and the solution was concentrated by a rotary evaporator. The concentrated sample was subjected to column chromatography with Hexane:Ethyl acetate to separate 2,2-difluoroethylacrylamide only, and then, the solvent was removed by the rotary evaporator, thereby obtaining a solid powder. The solid powder was further diluted in 5 mL of methylene chloride, followed by forming re-crystallized crystals in hexane. The solid powder generated by re-crystallization was dried in a vacuum oven at room temperature, thereby obtaining N-(2,2-difluoroethyl)acrylamide.

Preparative Example 4: Preparation of TFEAA

After adding 4.58 mL of 2,2,2-trifluoroethylamine, 10.3 mL of triethylamine and 50 mL of tetrahydrofuran to an one-neck round flask, the flask was placed in ice water. After diluting 6 mL of acryloyl chloride in 10 mL of tetrahydrofuran, this solution was slowly added drop wise to the flask while agitating the same. After completely adding the diluted solution thereto, the mixture was agitated at room temperature for 12 hours. After completing the reaction, the precipitate was filtered and the solution was concentrated by a rotary evaporator. The concentrated sample was subjected to column chromatography with Hexane:Ethyl acetate to separate N-(2,2,2-trifluoroethyl)acrylamide only, and then, the solvent was removed by the rotary evaporator, thereby obtaining a solid powder. The solid powder was dried in a vacuum oven at room temperature, thereby obtaining N-(2,2,2-trifluoroethyl)acrylamide.

Synthesis of Polymer

Preparative Example 5: Preparation of Poly(p-MS-BPAA)

3 mL of para-methylstyrene, 0.451 g of N-(4-benzoylphenyl)acrylamide and 0.0046 g of azobisisobutyronitrile were added to a 25 mL Schlenk round flask, followed by agitating the same. After repeating freeze-pump-thaw three times and blowing a nitrogen gas for 20 minutes, the flask was placed in an oil bath to conduct a reaction for 15 hours. After completing the reaction, the reaction product was filtered to extract a polymer, followed by drying the same in a vacuum oven at room temperature, thereby obtaining para-methylstyrene-N-(4-benzoylphenyl)acrylamide copolymer which has a structure unit represented by Formulae 1-1 and 2-1 below in a molar ratio of 100:8.

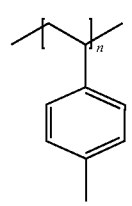

[Formula 1-1]

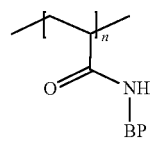

[Formula 2-1]

In Formula 2-1, BP denotes 4-benzoylphenyl.

Preparative Example 6: Preparation of Poly(FEAA-BPAA)

0.82 g of N-(2-fluoroethyl)acrylamide, 0.0176 g of N-(4-benzoylphenyl)acrylamide and 0.0023 g of azobisisobutyronitrile were added to a 25 mL Schlenk round flask, followed by agitating the same. After repeating freeze-pump-thaw three times and blowing a nitrogen gas for 20 minutes, the flask was placed in an oil bath to conduct a reaction for 15 hours. After completing the reaction, the reaction product was filtered to extract a polymer, followed by drying the same in a vacuum oven at room temperature, thereby obtaining (N-(2-fluoroethyl)acrylamide)-(N-(4-benzoylphenyl)acrylamide)copolymer which has a structure unit represented by Formulae 3-1 and 2-1 below in a molar ratio of 100:1.01.

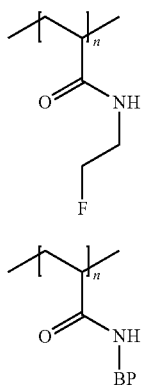

[Formula 3-1]

[Formula 2-1]

Preparative Example 7: Preparation of Poly(DFEAA-BPAP)

1.88 g of N-(2,2-difluoroethyl)acrylamide, 0.0351 g of N-(4-benzoylphenyl)acrylamide and 0.0046 g of azobisisobutyronitrile were added to a 25 mL Schlenk round flask, followed by agitating the same. After repeating freeze-pump-thaw about three times and blowing a nitrogen gas for 20 minutes, the flask was placed in an oil bath to conduct a reaction for 15 hours. After completing the reaction, the reaction product was filtered to extract a polymer, followed by drying the same in a vacuum oven at room temperature, thereby obtaining (N-(2,2-difluoroethyl) acrylamide)-(N-(4-benzoylphenyl)acrylamide)copolymer which has a structure unit represented by Formulae 3-2 and 2-1 below in a molar ratio of 100:1.01.

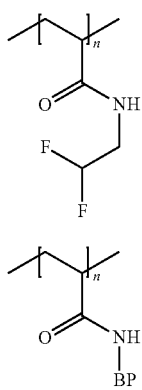

[Formula 3-2]

[Formula 2-1]

Preparative Example 8: Preparation of Poly(TFEAA-BPAA)

2.12 g of N-(2,2,2-trifluoroethyl)acrylamide, 0.0351 g of N-(4-benzoylphenyl)acrylamide and 0.0046 g of azobisisobutyronitrile were added to a 25 mL Schlenk round flask, followed by agitating the same. After repeating freeze-pump-thaw about three times and blowing a nitrogen gas for 20 minutes, the flask was placed in an oil bath to conduct a reaction for 15 hours. After completing the reaction, the reaction product was filtered to extract a polymer, followed by drying the same in a vacuum oven at room temperature, thereby obtaining (N-(2,2,2-trifluoroethyl)acrylamide)-(N-(4-benzoylphenyl)acrylamide)copolymer which has a structure unit represented by Formulae 3-3 and 2-1 below in a molar ratio of 100:1.01.

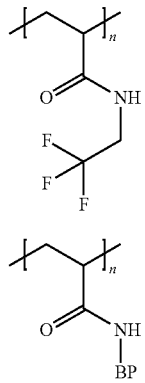

[Formula 3-3]

[Formula 2-1]

Details of physical properties of the polymers prepared in Preparative Examples 5 to 8 above are shown in Table 2 below:

TABLE 2

| | $Mn^{1)}$ (g/mol) | $PDI^{1)}$ | $Tg^{2)}$ | BPAA content$^{3)}$ (%) | Refractive index$^{4)}$ |
|---|---|---|---|---|---|
| Preparative Example 5 | 22,400 | 1.72 | 113° C. | 3.5% | 1.587 |
| Preparative Example 6 | 17,200 | 2.86 | 13° C. | 0.4% | 1.485 |
| Preparative Example 7 | 31,200 | 3.19 | 44° C. | 0.5% | 1.464 |
| Preparative Example 8 | 63,400 | 1.51 | 134° C. | 0.4% | 1.433 |

1) Mn (number average molecular weight) and PDI (Polydispersity Index): Determined by gel chromatography (GPC) using polystyrene as a standard sample for calibration.
2) Tg (glass transition temperature): Measured by a differential scanning calorimeter (DSC).
3) Content of N-(4-benzoylphenyl)acrylamide (BPAA) structure unit: Measured by NMR.
4) Refractive index: Measured by an ellipsometer.

Fabrication of Color-Conversion Photonic Crystal Structure

Example 1

By dissolving 0.02 g of the para-methylstyrene-N-(4-benzoylphenyl)acrylamide copolymer having a high refractive index prepared in Preparative Example 5 in toluene, a high refractive index dispersion composition was prepared. On the other hand, a low refractive index dispersion composition was prepared by dissolving 0.012 g of the (N-(2-fluoroethyl)acrylamide)-(N-(4-benzoylphenyl)acrylamide) copolymer having a low refractive index prepared in Preparative Example 6 in 1-ethanol. After applying the high refractive index dispersion composition to a glass substrate by a spin coater at 1300 rpm, the substrate was cured at 365 nm for 5 minutes to prepare a high refractive index layer with a thickness of 90 nm. The glass substrate having the high refractive index layer formed thereon was dipped in a toluene solution to remove the uncured part. After applying the low refractive index dispersion composition to the high refractive index layer by the spin coater at 1300 rpm, the treated substrate was cured at 365 nm for 5 minutes to prepare a low refractive index layer with a thickness of 63 nm. The glass substrate having both the high refractive index layer and the low refractive index layer formed thereon was dipped in 1-propanol solution to remove the uncured part. By laminating the high refractive index layer and the low refractive index layer, repeatedly, on the low refractive index layer, a photonic crystal structure including total 15 sheets of refractive index layers alternately laminated was fabricated.

Example 2

By dissolving 0.02 g of the para-methylstyrene-N-(4-benzoylphenyl)acrylamide copolymer having a high refractive index prepared in Preparative Example 5 in toluene, a high refractive index dispersion composition was prepared. On the other hand, a low refractive index dispersion composition was prepared by dissolving 0.012 g of the (N-(2,2-difluoroethyl)acrylamide)-(N-(4-benzoylphenyl)acrylamide)copolymer having a low refractive index prepared in Preparative Example 7 in 1-propanol. Thereafter, according to the same procedures as described in Example 1, a photonic crystal structure including total 15 sheets of high refractive index layers having a thickness of 90 nm and low refractive index layers having a thickness of 57 nm alternately laminated, was fabricated.

Example 3

By dissolving 0.02 g of the para-methylstyrene-N-(4-benzoylphenyl)acrylamide copolymer having a high refractive index prepared in Preparative Example 5 in toluene, a high refractive index dispersion composition was prepared. On the other hand, a low refractive index dispersion composition was prepared by dissolving 0.012 g of the (N-(2,2,2-trifluoroethyl)acrylamide)-(N-(4-benzoylphenyl)acrylamide)copolymer having a low refractive index prepared in Example 8 in 1-propanol. Thereafter, according to the same procedures as described in Example 1, a photonic crystal structure including total 15 sheets of high refractive index layers having a thickness of 90 nm and low refractive index layers having a thickness of 54 nm alternately laminated, was fabricated.

Example 4

According to the same procedures as described in Example 1, a photonic crystal structure including total 9 sheets of high refractive index layers having a thickness of 90 nm and low refractive index layers having a thickness of 63 nm alternately laminated, was fabricated.

The photonic crystal structures fabricated in the above examples are summarized in Table 3 below.

Experimental Example

Experimental Example 1: Observation of Color Conversion to Number of the Laminated Refractive Index Layers After exposing each of the color-conversion photonic crystal structures fabricated in Examples 1 to 4 to atmosphere (without external stimulation) and water, a reflective wavelength and specular reflection were measured by a reflectometer (USB 4000, Ocean Optics). Measured results are shown in Table 4 below.

TABLE 4

| | External stimulation | | | |
|---|---|---|---|---|
| | None | | Water | |
| Measured physical properties | Reflective wavelength (nm) | Specular reflection (%) | Reflective wavelength (nm) | Specular reflection (%) |
| Example 1 | 533 | 23 | 656 | 54 |
| Example 4 | 380 | 22 | 420 | 33 |

As shown in Table 4 above, it can be seen that the photonic crystal structure having total 15 refractive index layers fabricated in Example 1 exhibits higher specular reflection than the photonic crystal structure having total refractive index layers fabricated in Example 4, when being exposed to external stimulation. This fact means that, as the number of high refractive index layers and low refractive index layers alternately laminated is increased, constructive interference between partial reflective wavelengths at the interfaces between the layers is more strengthened, thus to increase an intensity of the reflective wavelength.

Figure 2:
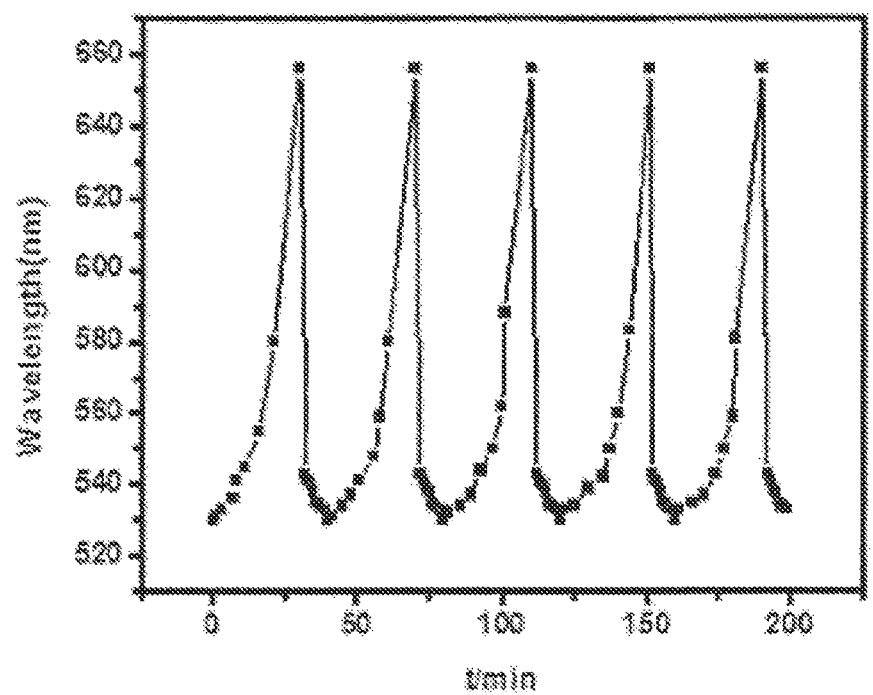
FIG. 2 illustrates test results of reproducibility to a change in relative humidity of the color-conversion photonic crystal structure fabricated in Example 1.
Figure 3:
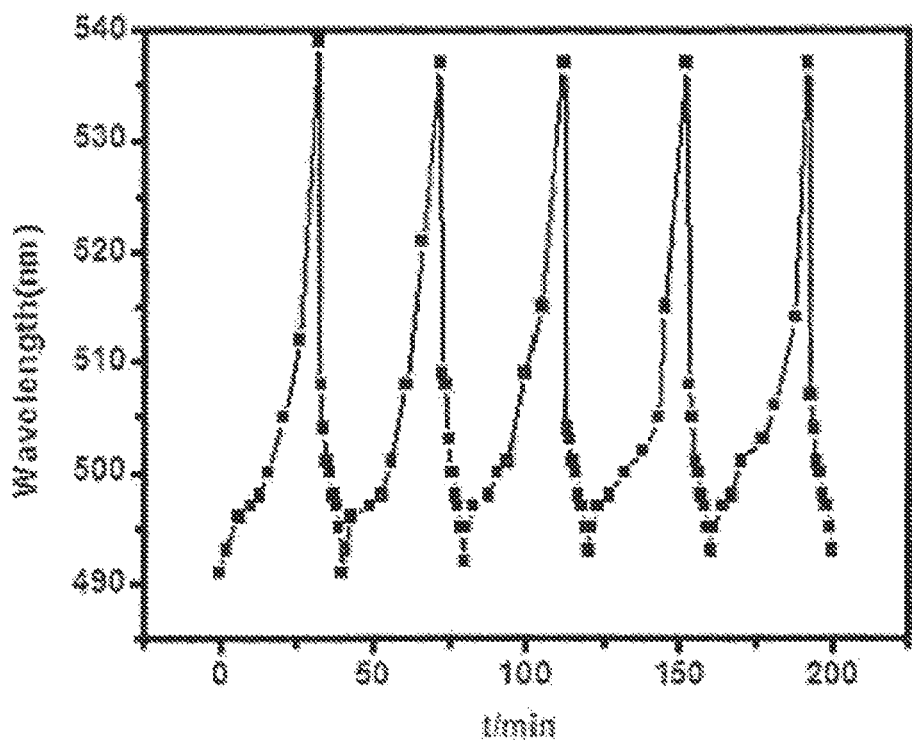
FIG. 3 illustrates test results of reproducibility to a change in relative humidity of the color-conversion photonic crystal structure fabricated in Example 2.

Experimental Example 2: Determination of Specular Reflection and Reproducibility Depending on Change in Humidity Each of the color-conversion photonic crystal structures fabricated in Examples 1 and 2 was subjected to measurement of specular reflection depending on a change in relative humidity (10% to 90%) and determination of reproducibility of the same by a reflectometer (USB 4000, Ocean Optics). Measured results of specular reflection are shown in Table 5 below, while results of determining reproducibility of the same in Examples 1 and 2 are illustrated in FIGS. 2 and 3, respectively.

TABLE 3

| | | High refractive index layer | | Low refractive index layer | | Total |
|---|---|---|---|---|---|---|
| | Substrate | Type of copolymer | Thickness (nm) | Type of copolymer | Thickness (nm) | number of lamination |
| Example 1 | Glass | Poly(p-MS-BPAA) | 90 | Poly(FEAA-BPAA) | 63 | 15 |
| Example 2 | Glass | Poly(p-MS-BPAA) | 90 | Poly(DFEAA-BPAA) | 57 | 15 |
| Example 3 | Glass | Poly(p-MS-BPAA) | 90 | Poly(TFEAA-BPAA) | 54 | 15 |
| Example 4 | Glass | Poly(-MS-BPAA) | 90 | Poly(FEAA-BPAA) | 63 | 9 |

TABLE 5

| Relative humidity (%) | Example 1 Reflective wavelength (nm) | Example 1 Specular reflection (%) | Example 2 Reflective wavelength (nm) | Example 2 Specular reflection (%) |
| --- | --- | --- | --- | --- |
| 10 | 530 | 24 | 485 | 20 |
| 20 | 533 | 23 | 488 | 19 |
| 30 | 537 | 24 | 489 | 19 |
| 40 | 545 | 26 | 493 | 20 |
| 50 | 553 | 28 | 494 | 20 |
| 60 | 564 | 32 | 495 | 20 |
| 70 | 584 | 38 | 505 | 21 |
| 80 | 628 | 51 | 522 | 20 |

As shown in Table 5 above, it can be seen that the color-conversion photonic crystal structures fabricated in Examples 1 and 2 exhibit marked shift of the reflective wavelength depending on a change in relative humidity, thus attaining excellent sensitivity to the change in humidity. Further, it can also be seen that the reflective wavelength of the color-conversion photonic crystal structure is shifted to be increased when increasing the relative humidity, and the specular reflection is also increased. Herein, since the shifted reflective wavelength corresponds to the visible light region, variation of the reflective wavelength of the photonic crystal structure could be visually observed.

Further, as shown in FIG. 2 and FIG. 3, the color-conversion photonic crystal structures fabricated in Examples 1 and 2 reflected light at a wavelength in the same range even though several cycles were repeated. This result means that the above color-conversion photonic crystal structure may attain superior reproducibility.

As such, it can be confirmed that the photonic crystal structure according to one embodiment of the present invention may be useable as a humidity sensor. Furthermore, it can also be confirmed that the humidity sensor manufactured using the above structure may easily and visually detect humidity and further exhibit excellent sensitivity and reproducibility.

Experimental Example 3: Measurement of Specular Reflection Depending on Change in a Concentration of Ethanol or Methanol Each of the color-conversion photonic crystal structures fabricated in Examples 1 and 3 was subjected to measurement of specular reflection depending on a change in a concentration of ethanol (5 ppm to 100 ppm) by a reflector meter (USB 4000, Ocean Optics), and measured results thereof are shown in Table 6 below. Further, each of the color-conversion photonic crystal structures fabricated in Examples 1 to 3 was subjected to measurement of specular reflection depending on a change in a concentration of methanol (5 ppm to 100 ppm) by the reflectometer (USB 4000, Ocean Optics), and measured results thereof are shown in Table 7 below.

TABLE 6

| Change in concentration of ethanol (ppm) | Example 1 Reflective wavelength (nm) | Example 1 Specular reflection (%) | Example 2 Reflective wavelength (nm) | Example 2 Specular reflection (%) | Example 3 Reflective wavelength (nm) | Example 3 Specular reflection (%) |
| --- | --- | --- | --- | --- | --- | --- |
| Pristine | 535 | 15 | 493 | 15 | 487 | 14 |
| 5 | 538 | 16 | 495 | 15 | 492 | 15 |
| 10 | 542 | 16 | 497 | 16 | 493 | 15 |
| 20 | 543 | 16 | 498 | 16 | 495 | 15 |
| 30 | 547 | 16 | 499 | 16 | 496 | 15 |
| 40 | 548 | 17 | 501 | 16 | 500 | 15 |
| 50 | 550 | 17 | 503 | 16 | 503 | 15 |
| 75 | 560 | 18 | 515 | 18 | 513 | 15 |
| 100 | 575 | 19 | 523 | 19 | 520 | 15 |

TABLE 7

| Change in concentration of methanol (ppm) | Example 1 Reflective wavelength (nm) | Example 1 Specular reflection (%) | Example 2 Reflective wavelength (nm) | Example 2 Specular reflection (%) | Example 3 Reflective wavelength (nm) | Example 3 Specular reflection (%) |
| --- | --- | --- | --- | --- | --- | --- |
| Pristine | 535 | 15 | 493 | 15 | 487 | 13 |
| 5 | 536 | 16 | 496 | 16 | 489 | 13 |
| 10 | 537 | 16 | 497 | 16 | 490 | 13 |
| 20 | 539 | 16 | 498 | 17 | 491 | 13 |
| 30 | 541 | 16 | 499 | 17 | 493 | 13 |
| 40 | 542 | 16 | 502 | 17 | 495 | 15 |
| 50 | 543 | 16 | 504 | 18 | 498 | 15 |
| 75 | 552 | 17 | 510 | 19 | 510 | 15 |
| 100 | 563 | 20 | 519 | 22 | 516 | 15 |

As shown in Tables 6 and 7 above, it can be seen that the color-conversion photonic crystal structures fabricated in Examples 1 to 3 exhibit marked shift of the reflective wavelength depending on a change in a concentration of ethanol or methanol, thus attaining excellent sensitivity depending on the change in a concentration of ethanol or methanol. Further, it can also be seen that the reflective wavelength of each of the color-conversion photonic crystal structures is shifted to be increased when increasing the relative humidity, and the specular reflection is also increased. Herein, since the shifted reflective wavelength corresponds to a visible light region, variation of the reflective wavelength of the photonic crystal structure could be visually observed.

As such, it can be confirmed that the photonic crystal structure according to one embodiment of the present invention may be usable as a sensor for detecting an organic solvent such as ethanol and methanol. Furthermore, it can also be confirmed that the organic solvent sensor manufactured using the above structure may easily and visually detect the organic solvent, thereby being useful for quantitative analysis of the organic solvent.

DESCRIPTION OF REFERENCE NUMERALS

1: Incident light
2: Reflected light
3: Transmitted light
10: Color-conversion photonic crystal structure
11: Substrate
13: First refractive index layer
15: Second refractive index layer

The invention claimed is:

1. A color-conversion photonic crystal structure, comprising:
a first refractive index layer which includes a first polymer having a first refractive index; and a second refractive index layer which includes a second polymer having a second refractive index, wherein these refractive index layers are alternately laminated,
wherein the first refractive index is higher than the second refractive index; and
the second polymer comprises a structure unit represented by Formula 3:

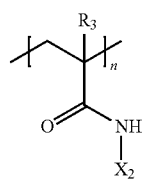

[Formula 3]

wherein $R_3$ is selected from hydrogen and $C_{1-3}$ alkyl;
$X_2$ is $C_{1-10}$ alkyl substituted by at least one fluorine atom; and
n is independently an integer of 1 or more.

2. The structure of claim 1, wherein a total laminating number of the first refractive index layer and the second refractive index layer ranges from 5 to 30.

3. The structure of claim 1, wherein the first refractive index layer has a thickness of 50 to 150 nm, and the second refractive index layer has a thickness of 5 to 80 nm.

4. The structure of claim 1, wherein the first polymer has a structure unit represented by Formulae 1 and 2 below in a molar ratio of 100:1 to 100:20, and a number average molecular weight of 10,000 to 100,000 g/mol:

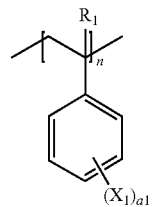

[Formula 1]

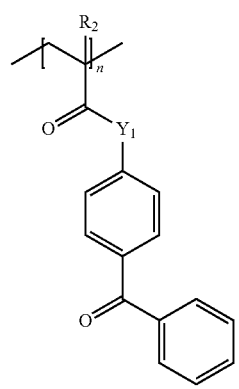

[Formula 2]

wherein $R_1$ and $R_2$ are each independently selected from hydrogen and $C_{1-3}$ alkyl;
$X_1$ is selected from hydroxyl, cyano, nitro, amino, sulfonic acid or salts thereof, $C_{1-10}$ alkyl and $C_{1-10}$ alkoxy;
a1 is selected from 0, 1, 2 and 3;
$Y_1$ is O or NH; and
n is independently an integer of 1 or more.

5. The structure of claim 4, wherein $X_1$ in Formula 1 is selected from methyl, ethyl, propyl, butyl, iso-butyl, sec-butyl and tert-butyl, and a1 is 0 or 1.

6. The structure of claim 1, wherein the second polymer has the structure unit represented by Formula 3 and a structure unit represented by Formula 4 in a molar ratio of 100:1 to 100:5, and a number average molecular weight of 10,000 to 100,000 g/mol:

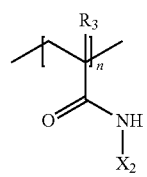

[Formual 3]

[Formula 4]

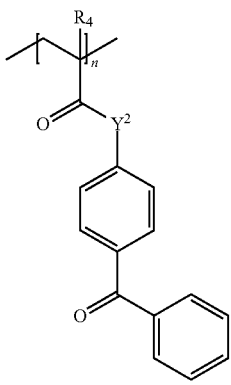

wherein R₃ and R₄ are each independently selected from hydrogen and $C_{1-3}$ alkyl;

X₂ is selected from $C_{1-10}$ alkyl substituted by at least one fluorine atom;

Y₂ is O or NH; and n is independently an integer of 1 or more.

7. The structure of claim 6, wherein X₂ in Formula 3 is selected from fluoromethyl, difluoromethyl, trifluoromethyl, 1-fluoroethyl, 2-fluoroethyl, 1,1-difluoroethyl, 1,2-difluoroethyl, 2,2-difluoroethyl, 1,1,2-trifluoroethyl, 1,2,2-trifluoroethyl, 1,1-trifluoroethyl, 1-fluoropropyl, 2-fluoropropyl, 1,1-difluoropropyl, 1,2-difluoropropyl, 2,2-difluoropropyl, 1,1,2-trifluoropropyl, 1,2,2-trifluoropropyl, 1-fluorobutyl, 2-fluorobutyl, 1,1-difluorobutyl, 1,2-difluorobutyl, 2,2-difluorobutyl, 1,1,2-trifluorobutyl; and 1,2,2-trifluorobutyl.

8. The structure of claim 1, wherein a reflective wavelength of the photonic crystal structure is shifted by an external stimulation.

9. The structure of claim 8, wherein the external stimulation occurs by a change in humidity or organic solvent concentration.

10. A color-conversion photonic crystal sensor comprising the color-conversion photonic crystal structure of claim 1.

* * * * *